United States Patent
Davis

[19]

[11] Patent Number: 6,123,069
[45] Date of Patent: Sep. 26, 2000

[54] OXYGEN BREATHING SYSTEM WITH PROGRAMMED OXYGEN DELIVERY

[76] Inventor: James E. P. Davis, 2510 Arizona Ave., #8, Santa Monica, Calif. 90404

[21] Appl. No.: 08/152,475

[22] Filed: Nov. 15, 1993

[51] Int. Cl.[7] .................................................. A61M 15/00
[52] U.S. Cl. ............................... 128/202.26; 128/205.12; 128/205.28
[58] Field of Search .................... 128/202.26, 204.18, 128/204.15, 204.16, 205.11, 205.12, 205.22, 205.28

[56] References Cited

U.S. PATENT DOCUMENTS

| | | | |
|---|---|---|---|
| 980,996 | 1/1911 | Parker | 128/202.26 |
| 1,003,935 | 9/1911 | Merryman | 128/202.26 |
| 1,201,565 | 10/1916 | Davidson | 128/202.26 |
| 3,129,707 | 4/1964 | Becker et al. | 128/205.13 |
| 3,615,252 | 10/1971 | DiPietro | 128/202.26 |
| 3,736,104 | 5/1973 | Churchill et al. | 128/202.26 |
| 3,737,287 | 6/1973 | Churchill et al. | 128/202.26 |
| 3,815,592 | 6/1974 | Staub | 128/202.26 |
| 3,861,880 | 1/1975 | Thompson | 128/202.26 |
| 4,019,509 | 4/1977 | Li et al. | 128/202.26 |
| 4,157,091 | 6/1979 | Pampuch | 128/202.26 |
| 4,278,637 | 7/1981 | McBride | 128/202.26 |
| 4,292,967 | 10/1981 | Pasternack | 128/202.26 |
| 4,362,153 | 12/1982 | Wilson et al. | 128/202.26 |
| 4,459,981 | 7/1984 | Mascher et al. | 128/202.26 |
| 4,506,667 | 3/1985 | Ansite | 128/204.25 |
| 4,526,758 | 7/1985 | Alengoz et al. | 128/202.26 |
| 4,548,730 | 10/1985 | Koslow | 128/202.26 |
| 4,811,732 | 3/1989 | Hartung | 128/204.26 |
| 5,036,841 | 8/1991 | Hamilton | 128/202.26 |
| 5,048,517 | 9/1991 | Pasternack | 128/205.28 |
| 5,072,728 | 12/1991 | Pasternack | 128/204.18 |
| 5,076,267 | 12/1991 | Pasternack | 128/205.22 |

FOREIGN PATENT DOCUMENTS

| | | | |
|---|---|---|---|
| 189738 | 4/1906 | Germany | 128/202.26 |
| 8602063 | 4/1986 | WIPO | 128/202.26 |

OTHER PUBLICATIONS

Hawley's Condensed Chemical Dictionary; 11th ed.; Sax et al, ed's.; Van Nostrand Reinhold Co., NY; ISBN 0–442–28097–1. ©1987, pp. 864,1068, & 1069.

*Primary Examiner*—Aaron J. Lewis
*Attorney, Agent, or Firm*—Robert E. Malm

[57] ABSTRACT

The oxygen breathing system with programmed oxygen delivery comprises a breathing circuit which a user exhales into and inhales from and a source of oxygen which delivers oxygen to the breathing circuit at a programmed rate. The oxygen is supplied at a high rate during the initial period of operation and at a low rate during the remaining period of operation. An overpressure relief valve in the breathing circuit opens during the initial time period because of the high oxygen delivery rate thereby flushing from the breathing circuit the nitrogen initially residing in the lungs of the user and in the breathing circuit. As a result of the flushing, the oxygen content in the breathing circuit approaches 100 percent at the end of the initial period and remains near this level during the subsequent time period. The source of oxygen can be a chemical reaction which occurs when a chemical compound is combined with a liquid in which case the programmed oxygen delivery is achieved by metering the liquid that is added to the chemical compound. Alternatively, the source of oxygen can be a storage container of oxygen or a contained chemical reaction and the programmed oxygen delivery is accomplished with a valve having a programmed flow rate.

20 Claims, 1 Drawing Sheet

OXYGEN BREATHING SYSTEM WITH PROGRAMMED OXYGEN DELIVERY

BACKGROUND OF INVENTION

This invention relates generally to self-contained oxygen breathing apparatus and more particularly to breathing apparatus intended for medical application.

It is believed that up to 11.5 million people in the United States suffer intermittently with some form of migraine headache, the most common type of vascular headache. Historically, drug treatments have been less than 50% effective and have had strong negative side effects. Glaxo's "Sumatriptan", newly approved by the Federal Drug Administration, seems to be a great improvement. It may reduce headache pain in 75% of patients in one or two hours, and has fewer side effects than earlier drugs.

Overlooked or neglected since its discovery as a migraine treatment more than half a century ago is the administration of pure oxygen to the patient. It is well documented that oxygen relieves most cluster headaches within 30 minutes with absolutely no side effects. This form of treatment hasn't been popular with most physicians because of the inconvenience and expense of oxygen delivery from a cylinder.

The satisfaction of the need of migraine sufferers for more convenient and less expensive oxygen delivery systems depends on finding a suitable chemical reaction for generating oxygen that utilizes low-cost chemicals and an associated low-cost apparatus for containing the chemical reaction and delivering the oxygen to a face mask.

One possible source of oxygen are the chlorates and perchlorates of lithium, sodium, and potassium, which give off oxygen when heated. Chlorate candles, a combination of the oxygen-producing material, a fuel, a material that absorbs trace amounts of chlorine, and an inert binder, have been used as oxygen sources in submarines and airplanes and have many desirable characteristics. Unfortunately, they are not inexpensive.

The peroxides of sodium and potassium in combination with carbon dioxide and water vapor decompose into oxygen and water vapor. A catalyst such as nickel sulfate is required to obtain total decomposition of the peroxides. A conceptually-simple oxygen breathing system is obtained by circulating the exhaled breath of a user through the peroxide and back to the user for inhalation.

The peroxides have the advantage of not only producing oxygen but also absorbing the carbon dioxide in the user's exhaled breath. The peroxides are not very oxygen-weight efficient and breathing apparatus based on peroxides are usually supplemented with bottled oxygen.

The alkali metal superoxides react with water vapor to form oxygen and the metal hydroxide. The metal hydroxide reacts with carbon dioxide to form the carbonate, the bicarbonate, and water vapor.

The superoxides also have the advantage of generating oxygen and absorbing carbon dioxide. Breathing apparatus based on the superoxides do not require any auxiliary source of oxygen.

Sodium percarbonate when combined with water and a catalyst such as manganese dioxide decomposes into sodium carbonate, oxygen, and water. Since this reaction is strongly exothermic, the oxygen is released at high temperature and part of the water is turned into steam.

The oxygen produced in this way cannot be directly used for human respiration because of its high temperature and excessive humidity. Consequently, any breathing apparatus based on this chemical reaction must incorporate a heat exchanger to cool the oxygen.

Breathing apparatus based on the above-described chemical reactions are beyond the reach of most migraine sufferers either because of the cost of chemicals or the cost of the apparatus necessary to support the chemical reaction.

BRIEF SUMMARY OF INVENTION

The oxygen breathing system with programmed oxygen delivery comprises a breathing circuit into and out of which a user exhales and inhales and a source of oxygen with a programmed flow of oxygen.

The exhaled gases from the user's lungs are combined with the programmed flow of oxygen and then returned to the user for inhalation. The oxygen is delivered to the breathing circuit at a high flow rate during an initial period of use and at a low flow rate during a subsequent time period. The high flow rate during the initial time period causes an overpressure relief valve in the breathing circuit to open and dump a substantial portion of the mixture of exhaled gases and oxygen from the breathing circuit during the initial time period. As a result, the large quantity of nitrogen that initially resides in the user's blood, lungs, and the breathing circuit is eliminated so that the oxygen content in the breathing circuit approaches 100 percent by the end of the initial period.

The oxygen flow rate during the subsequent time period is sufficiently low that the overpressure relief valve remains closed thereby conserving the oxygen being supplied to the breathing circuit.

The programmed delivery of oxygen is achieved in one of two ways, depending on the source of oxygen. If the source of oxygen is a chemical reaction that occurs when a chemical compound is combined with a liquid, controlling the rate of delivery of the liquid to the chemical compound results in a controlled delivery of oxygen. If the source of oxygen is a storage cylinder or a contained chemical reaction not involving the combination of a chemical compound with a liquid, the controlled delivery of oxygen is accomplished with a programmed flow rate valve.

DESCRIPTION OF THE PREFERRED EMBODIMENT

Figure 1:
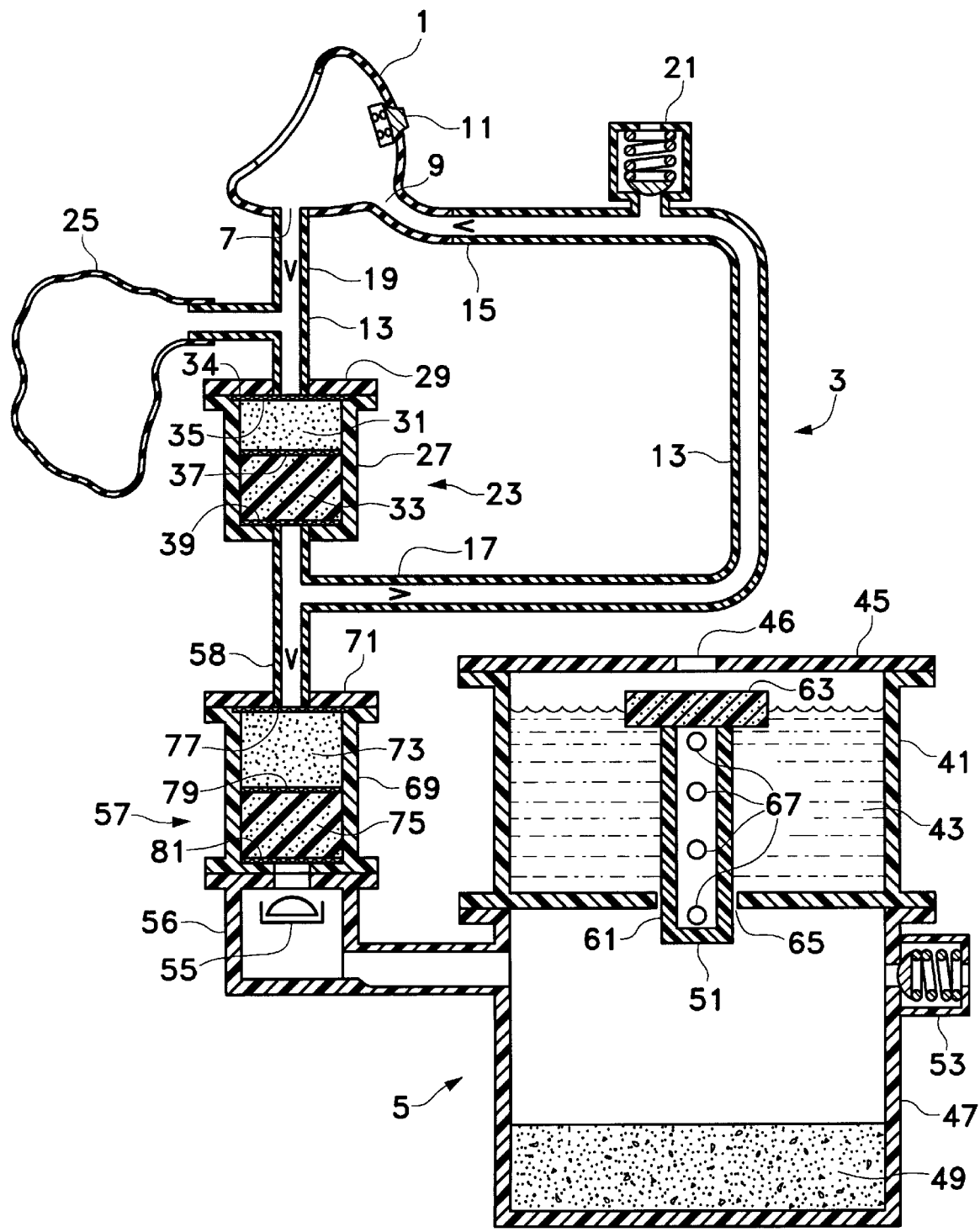
FIG. 1 is sectional view of the preferred embodiment of the oxygen breathing apparatus with programmed oxygen delivery.

Heavy cylinders and valves or complicated systems based on chemical reactions are usually used to supply oxygen for human breathing in hazardous environments and medical emergencies. This invention provides a means for supplying oxygen that is smaller, lighter, and less complicated than prior systems. Thus, the system is particularly appropriate for those situations where portability and cost are preeminent considerations.

The preferred embodiment of the invention is structured to provide a 30-minute supply of oxygen because this length of time is appropriate for many common medical situations. Other durations can be obtained simply by scaling container volumes.

It would be possible for a person to breathe 100 percent oxygen by breathing into a breath-circulating apparatus provided with a source of oxygen and containing chemicals to absorb carbon dioxide and water vapor, were it not for the existence of nitrogen in the person's lungs and blood stream. Without some mechanism for disposing of this major constituent, the oxygen content is prevented from rising to more than 50 percent of the gas content of the breath-circulating apparatus.

Since the time required to exhaust all of the nitrogen from a person's lungs when the person is breathing 100 percent oxygen is about 5 to 10 minutes, equivalent to about 50 to 100 breaths, oversupplying oxygen for the entire 30-minute oxygen supply time is unnecessary and wasteful.

In order to approach the desired 100 percent oxygen level in the breath-circulating apparatus using minimum quantities of chemicals, an excess of oxygen is generated during an initial period and used to flush the nitrogen out of the breath-circulating apparatus. The generation of oxygen is reduced after this initial period to a level adequate to serve the metabolic needs of the person using the system.

In one preferred embodiment, oxygen is generated at a 5-liter-per-minute rate during the first 10 minutes of operation and then at a 1-liter-per-minute rate for the last 20 minutes. The 1-liter-per-minute rate is more than the metabolic demand for the largest person and consequently, the oxygen supply during the last 20 minutes of operation is more than adequate.

In another preferred embodiment, oxygen is generated at a constant 5-liter-per-minute rate—a mode of operation which may be preferable if there is any likelihood that nitrogen could be reintroduced into the breathing circuit during operation.

Other oxygen delivery programs, which are easily realizable with this invention, may prove useful in other situations.

A sectional view of the preferred embodiment of the oxygen breathing system is shown in FIG. 1. The breathing system is comprised of the face mask 1, the breathing circuit 3, and the oxygen generator 5.

The face mask 1 is designed to intimately mate with the human face so that air inhaled into or exhaled out of the user's lungs is constrained to enter and exit the face mask through orifices 7 and 9. A suction relief valve 11 is provided so that outside air may be inhaled if the amount of air available through the orifices is insufficient.

An alternative to the face mask that may be appropriate under certain circumstances is a nose clip which constrains the user to breathing through his mouth and a mouthpiece which terminates in the two orifices 7 and 9.

The two orifices 7 and 9 of the face mask 1 connect to the breathing circuit 3 which provides a closed passageway for the exhaled breath of the user, after appropriate processing, to return to the face mask for subsequent inhalation. The breathing circuit consists of flexible plastic hoses 13, check valves 15, 17, and 19, relief valve 21, gas absorption canister 23, and flexible breathing bag 25.

The flexible plastic hoses 13 are approximately two centimeters in diameter. The check valves 15, 17, and 19, well known in the art, restrict the flow to one direction thereby constraining gases exiting from the face mask 1 to traverse the breathing circuit 3 in a clockwise direction.

The spring-loaded relief valve 21, also well known in the art, vents the breathing circuit 3 when the pressure within the breathing circuit exceeds one centimeter of water.

The gas absorption canister 23 is comprised of a plastic cylindrical container 27 and a plastic cover 29, the plastic cover being fastened to the container by means of spring clips or other appropriate means. A gasket at the interface of the container and cover, not shown, provides a gas-tight seal. The canister 23 contains 350 cubic centimeters of soda lime 31, a carbon dioxide absorber, and 100 cubic centimeters of silica gel 33, a water vapor absorber.

Standard respiratory breathing filter paper 34 prevents particulate matter greater than 0.3 micrometers from entering the users lungs. The two absorbers are kept separated and within the canister by means of fine-mesh screens 35, 37, and 39. The two absorbers are about 3 to 8 mesh so that there is low breathing resistance in the breathing circuit 3.

The breathing bag 25 is made of a thin gas-impervious plastic or rubber material and expands and contracts as the user breaths thereby maintaining the pressure in the breathing circuit 3 at an approximately constant level. The breathing bag when fully expanded has a capacity of two liters.

The oxygen generator 5 generates oxygen by adding water to sodium perborate anhydrous ($NaBO_3$) in accordance with the chemical reaction

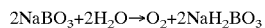

$$2NaBO_3 + 2H_2O \rightarrow O_2 + 2NaH_2BO_3$$

Methods of manufacturing sodium perborate anhydrous have been described in U.S. Pat. No. 3,421,842.

Theoretically, only 18 percent mole weight of water is required for this reaction. However, since $NaBO_3$ is a hygroscopic, low density powder, a much larger supply of water is required to get successful mixing and smooth generation of oxygen. Moreover, to achieve a constant rate of generation of oxygen over time, the rate at which water is added to the perborate must increase with time.

A surfactant is added to the perborate to facilitate mixing of the water and the perborate and to reduce foam where the reactants interface.

The oxygen generator 5 is comprised of water container 41 holding 1.8 liters of water 43, cover 45, chemical container 47 holding a mixture 49 of 800 grams of sodium perborate anhydrous and five grams of surfactant, float valve 51, pressure relief valve 53, liquid float check valve 55, gas absorption canister 57, and check valve 59.

Cover 45 is attached to water container 41 which in turn is attached to chemical container 47, the means of attachment in both cases being spring clips (not shown) or other appropriate means. A hole 46 in the cover can be utilized for filling the water container 41 with water. A gas-tight seal between the water container and the chemical container is obtained by means of a gasket (not shown).

The float valve 51 consists of a plastic pipe 61 closed at one end and fastened at the other end to a disc 63 made of polyfoam. The polyfoam disc is dimensioned such that the weight of the water it displaces exceeds the weight of the pipe, thereby causing the pipe to be suspended in the water. The diameter of the pipe is approximately 6.4 millimeters in diameter and of sufficient length to pass through the hole 65 in the bottom of water container 41 when suspended in 1.8 liters of water. The hole 65 is approximately 0.18 millimeter larger in diameter than the pipe 61.

There are holes 67 spaced at intervals along the length of the pipe 61 that control the flow rate of water from the water container 41 to the chemical container 47 as a function of water level in the water container (and time).

Water flows from water container 41 to chemical container 47 by two routes. One route is through the clearance region between pipe 61 and hole 65. The second route is through any hole 67 that is accessible to water in water container 41, down the pipe interior, and through any hole 67 that provides access to chemical container 47. As the water drains out of the water container and into the chemical container, the accessibility of the holes to the two containers changes thereby changing over time the rate at which water enters the chemical container.

A hole arrangement that results in a high oxygen generating rate initially and a lower rate subsequently is as follows: for a pipe 61 having a length of 67.3 units, a 1.5-mm-diameter hole 3.8 units from the distal end and a 1.5-mm-diameter hole 49.5 units from the distal end.

With this hole arrangement, the water flow rate into chemical container 47 is about 170 cubic centimeters per minute for the first 7.5 minutes (one hole in water container, the other in chemical container) and then decreases to about 20 cubic centimeters per minute (both holes in chemical container). The flow rate decreases slightly from this level over the remaining 20 minutes that it takes for the water to drain into the chemical container.

The corresponding oxygen generating rate is approximately 5 liters per minute for the first 10 minutes and then drops in a period of about 5 minutes to approximately 1 liter per minute. This hole arrangement results in the delivery of enough oxygen during the first 10 minutes of operation to flush the nitrogen from the lungs of the user and the breathing circuit 3 and provides enough oxygen during the last 20 minutes of operation to satisfy the metabolic needs of the user. It also permits this performance to be achieved with minimum quantities of chemicals and is, for this reason, the preferred hole arrangement.

The "step-function" delivery of oxygen may be unsatisfactory if the user is prone to coughing or taking off his face mask intermittently in order to talk. Such occurrences will result in nitrogen once again being drawn into the user's lungs and the one-liter-per-minute oxygen delivery rate during the last 20 minutes of operation will be inadequate to flush this nitrogen from the breathing system thereby sacrificing the near-100-percent oxygen content of the breathing gas that the system is designed to supply. In such cases, it may be preferable to utilize larger quantities of chemicals and supply a constant 5-liter-per-minute oxygen delivery rate for the entire operating period of the system.

An example of a hole pattern that results in an approximately constant oxygen generating rate is as follows: for a pipe 61 having a length of 119.4 units, a 1.0-mm-diameter hole 12.7 units from the distal end (the end furthest from the float 63), three 0.71-mm-diameter holes 71.1 units from the distal end, and four 2.3-mm-diameter holes equally-spaced around the circumference of the pipe and 119.4 units from the distal end.

With this hole arrangement, the water flow rate into chemical container 47 begins at 100 cubic centimeters per minute and ends at 170 cubic centimeters per minute. The oxygen generating rate remains approximately constant at about 5 liters per minute as the water empties into the chemical container 47.

Movement of the oxygen generator 5 can result in the water-perborate mixture foaming and oxygen being generated at an excessive rate. The relief valve 53 is provided to relieve any pressures in excess of 10 centimeters of water in the chemical container 47.

When stability returns to the oxygen generator 5, the surfactants contained in the chemical container 47 immediately suppress the foaming and return the oxygen generation to a normal output rate controlled by the water supply rate.

The oxygen generated in chemical container 47 flows through float check valve 55, gas absorption canister 57, and check valve 59 and into the breathing circuit 3. The float check valve 55 closes if the reactants in chemical container 47 foam and rise up and fill the float check valve chamber 56.

The gas absorption canister 57 is comprised of a plastic cylindrical container 69 and a plastic cover 71, the plastic cover being fastened to the container by means of spring clips. A gasket at the interface of the container and cover, not shown, provides a gas-tight seal. The canister 57 contains 50 cubic centimeters of activated charcoal 73, an odor absorber, and 200 cubic centimeters of silica gel 75, a water vapor absorber. The two absorbers are kept separated and within the canister by means of fine-mesh screens 77, 79, and 81. The two absorbers are about 3 to 8 mesh so as to minimize the resistance to the flow of oxygen.

The check valve 59 prevents the user's breaths from entering the oxygen generator 5.

In describing how the oxygen breathing system described herein is used, it is assumed that the various required chemicals are already in place. To use the system, the user fills the container 41 with water through the hole 46 in the cover 45. The user then places the face mask over his nose and mouth and begins breathing through the mask.

The oxygen generation rate during the first 10 minutes of operation is approximately 5 liters per minute. Any generation rate greater than 1 liter per minute causes the relief valve 21 to open and flush excess gases from the system. Thus, the system is being continually flushed during the first 10 minutes of operation.

The initial gas mixture in the breathing circuit 3 is ambient air which is approximately 21 percent oxygen, 79 percent nitrogen, and a fractional percentage of water vapor. Within approximately 5 minutes after breathing on the face mask 1 begins, the inhaled gas will exceed 90 percent oxygen and approach 100 percent after 10 minutes.

At the 10 minute point, the oxygen generation rate decreases to 1 liter per minute, sufficient to satisfy the metabolic needs of the user, and the inhaled gas remains near 100 percent oxygen for the remaining 20 minutes of operation.

During system operation, the activated charcoal 73 deodorizes and the silica gel 75 drys the 80 liters of generated oxygen. The soda lime 31 absorbs carbon dioxide and the silica gel 33 absorbs water vapor produced by the user's body. Small and physiologically-acceptable quantities of carbon dioxide and water vapor, the amounts depending on the user breathing rate and the quantities of absorbents used, remain in the breathing circuit 3 after the initial 10-minute flush period.

Approximately 30 minutes after use of the system was initiated, the oxygen generation process will abruptly cease and the breathing bag 25 will abruptly collapse, making it impossible for the user to inhale gas. The user must then remove the face mask 1, having reached the end of the 30-minute oxygen supply period. If the user fails to remove the face mask, the suction relief valve 11 opens, thereby allowing the user to breathe.

If the user coughs while wearing the face mask 1, relief valve 21 opens, thereby relieving the resulting overpressure in the breathing circuit 3.

The advantages of breathing pure oxygen can also be obtained with an alternative to the breathing system of FIG. 1 wherein a cylinder of oxygen or a chlorate candle having a time-controlled flow-rate valve is substituted for the oxygen generator 5. When operation of the system is initiated, the flow-rate valve delivers oxygen to the breathing circuit 3 at a 5-liter-per-minute rate. A spring-powered timer causes the flow-rate valve to deliver oxygen at a 1-liter-per-minute rate after 10 minutes have passed.

By using an electrically-controlled flow-rate valve capable of delivering a range of flow rates together with a controller, an arbitrary flow rate of oxygen as a function of time can be supplied to the breathing circuit 3.

What is claimed is:

1. An oxygen breathing system comprising:
    a means by which a user exhales gases into and inhales gases out of the system;
    a breathing circuit for receiving the exhaled gases from the user and delivering a mixture of some of the exhaled gases and oxygen to the user when the user inhales, the breathing circuit having an inlet for receiving the oxygen; and
    a means for supplying oxygen through the inlet to the breathing circuit at a delivery rate that varies with time from an initial rate to a final rate.

2. The oxygen breathing system of claim 1 wherein the oxygen supplying means is an oxygen generator, the generation resulting from a chemical reaction.

3. The oxygen breathing system of claim 2 wherein the chemical reaction is between a chemical compound and a liquid, the oxygen generator comprising:
    a liquid container having an outlet through which the liquid can flow;
    a reactor wherein the chemical reaction takes place, the reactor having a space for receiving the chemical compound, the reactor having an inlet through which the liquid can flow into the space occupied by the chemical compound, the reactor inlet being connected to the liquid container outlet, the reactor having an outlet for the gases generated as a result of the chemical reaction to exit the reactor, the outlet of the reactor being connected to the inlet of the breathing circuit; and
    a means for controlling the flow of liquid from the liquid container to the reactor in accordance with a predetermined function of time.

4. The oxygen breathing system of claim 3 wherein the chemical compound is sodium perborate anhydrous ($NaBO_3$) and the liquid is water.

5. The oxygen breathing system of claim 3 wherein the flow of liquid from the liquid container to the reactor occurs as a result of gravity, the liquid flow controlling means comprising:
    a pipe fastened at one end to a float and closed at the other end, the float causing the pipe to be vertically suspended in the liquid with the proximal end of the pipe near the surface of the liquid, the pipe having holes through the pipe wall at at least two levels, a level being a predetermined distance from the distal end of the pipe, there being at least one hole on the circumference of the pipe at each of the levels, the cross-sectional shape of the pipe transverse to the pipe axis being the same as the outlet of the liquid container, the pipe and the outlet being so arranged that the pipe can slide freely through the outlet as the level of the liquid in the liquid container decreases.

6. The oxygen breathing system of claim 3 wherein the reactor comprises:
    a gas absorption device which absorbs at least a portion of at least one undesired gas that is produced as a result of the chemical reaction, the gases produced as a result of the chemical reaction having to flow through the gas absorption device to reach the reactor outlet.

7. The oxygen breathing system of claim 6 wherein the gas absorption device comprises;
    an odor absorber; and
    a water vapor absorber.

8. The oxygen breathing system of claim 3 wherein the reactor comprises:
    a flow rate limit valve which limits the flow rate of gases exiting the reactor via the reactor outlet; and
    an overpressure relief valve which provides an exit for gases in the reactor when the gas pressure in the reactor exceeds a predetermined level.

9. The oxygen breathing system of claim 8 wherein the reactor further comprises:
    a check valve which prevents gases from entering the reactor through the reactor outlet.

10. A method of using the system of claim 3 comprising the steps:
    placing sodium perborate anhydrous ($NaBO_3$) in the reactor;
    placing water in the liquid container; and
    exhaling into and inhaling from the breathing circuit.

11. The oxygen breathing system of claim 1 wherein the breathing circuit comprises:
    an overpressure relief valve which provides an exit for gases in the breathing circuit when the oxygen delivery rate into the breathing circuit exceeds a predetermined level.

12. The oxygen breathing system of claim 11 wherein the predetermined oxygen delivery rate exceeds the predetermined level during an initial time period and does not exceed the predetermined level during a subsequent time period thereby causing the oxygen content of the breathing circuit to approach 100 percent by the end of the initial time period and to remain near this level during the subsequent time period.

13. The oxygen breathing system of claim 1 wherein the oxygen supplying means is an oxygen storage and delivery apparatus.

14. The oxygen breathing system of claim 13 wherein the oxygen storage and delivery apparatus comprises:
    an oxygen cylinder for storing oxygen; and
    a programmed flow rate valve attached to the oxygen cylinder, the flow rate valve having an outlet that connects to the inlet of the breathing circuit, the programming of the flow rate valve being such that the oxygen delivery rate is the predetermined function of time.

15. The oxygen breathing system of claim 14 wherein the programmed flow rate valve comprises:
    a controllable flow rate valve; and
    a controller that causes the oxygen delivery rate through the controllable flow rate valve to be in accordance with the predetermined function of time.

16. An oxygen breathing system comprising:
    a means by which a user exhales gases into and inhales gases out of the system;
    a breathing circuit for receiving the exhaled gases from the user and delivering a mixture of some of the exhaled gases and oxygen to the user when the user inhales, the breathing circuit having an inlet for receiving the oxygen; and
    a means for supplying oxygen through the inlet to the breathing circuit, the oxygen being obtained by combining sodium perborate anhydrous ($NaBO_3$) and water.

17. The oxygen breathing system of claim 16 wherein the sodium perborate anhydrous is combined with a surfactant, thereby generating oxygen without foaming.

18. A method for supplying a person with oxygen for breathing, the oxygen being obtained by means of a chemical reaction, the method comprising the steps:

receiving the gases exhaled by the person;

providing a flow of oxygen at a rate that varies with time from an initial oxygen-flow rate to a final oxygen-flow rate by adding a liquid to a chemical compound at a rate that varies with time from an initial liquid-flow rate to a final liquid-flow rate, the chemical reaction between the liquid and the chemical compound resulting in the generation of oxygen at a rate that varies with time from the initial oxygen-flow rate to the final oxygen-flow rate;

mixing the exhaled gases and the oxygen; and supplying the mixture of exhaled gases and oxygen to the person for inhalation.

19. A method for supplying a person with oxygen for breathing, the oxygen being obtained by means of a chemical reaction, the method comprising the steps:

receiving the gases exhaled by the person;

providing a flow of oxygen at a rate that varies with time from an initial oxygen-flow rate to a final oxygen-flow rate;

mixing the exhaled gases and the oxygen;

supplying the mixture of exhaled gases and oxygen to the person for inhalation;

removing at least a portion of at least one undesired gas, at least a portion of the odorous gases and at least a portion of the water vapor that accompany the oxygen.

20. A method for supplying a person with oxygen for breathing comprising the steps:

receiving the gases exhaled by the person;

providing a flow of oxygen at a rate that varies with time from an initial oxygen-flow rate to a final oxygen-flow rate;

mixing the exhaled gases and the oxygen; and supplying the mixture of exhaled gases and oxygen to the person for inhalation;

wherein oxygen is provided at a rate that exceeds a predetermined level during an initial time period and does not exceed the predetermined level during a subsequent time period, the method further comprising the step:

discarding a portion of the mixture of exhaled gases and oxygen during the time period when the oxygen is generated at a rate that exceeds the predetermined level thereby causing the oxygen content of the gas mixture supplied to the person for inhalation to approach 100 percent by the end of the initial time period and to remain near this level during the subsequent time period.

* * * * *